United States Patent [19]

Bristol et al.

[11] Patent Number: 4,657,897

[45] Date of Patent: Apr. 14, 1987

[54] N6-SUBSTITUTED ADENOSINES FOR TREATING PAIN

[75] Inventors: James A. Bristol; Walter H. Moos, both of Ann Arbor; Bharat Trivedi, Canton, all of Mich.

[73] Assignee: Warner-Lambert Company, Morris Plains, N.J.

[21] Appl. No.: 756,004

[22] Filed: Jul. 17, 1985

Related U.S. Application Data

[60] Division of Ser. No. 621,943, Jun. 22, 1984, abandoned, which is a continuation-in-part of Ser. No. 519,284, Aug. 1, 1983, abandoned.

[51] Int. Cl.$^4$ .................... A61K 31/70; C07H 19/20; C07H 19/167
[52] U.S. Cl. ..................................... 514/47; 514/46; 536/26; 536/27
[58] Field of Search .................. 536/26; 514/47, 46

[56] References Cited

U.S. PATENT DOCUMENTS

| | | | |
|---|---|---|---|
| 3,551,409 | 12/1970 | Kampe et al. | 536/26 |
| 4,373,097 | 2/1983 | Stramentinoli et al. | 514/46 |

FOREIGN PATENT DOCUMENTS

| | | | |
|---|---|---|---|
| 0139358 | 5/1985 | European Pat. Off. | 514/47 |
| 2406587 | 8/1975 | Fed. Rep. of Germany | 536/26 |
| 2426682 | 12/1975 | Fed. Rep. of Germany | 536/26 |

*Primary Examiner*—Johnnie R. Brown
*Attorney, Agent, or Firm*—Joan Thierstein

[57] ABSTRACT

N6-Substituted diarylalkyladenosines and pharmaceutically acceptable acid addition salts having highly desirable central nervous system and cardiovascular properties, processes for their manufacture and pharmaceutical compositions and methods for using said compounds and compositions are described.

12 Claims, No Drawings

N6-SUBSTITUTED ADENOSINES FOR TREATING PAIN

This is a division of application U.S. Ser. No. 621,943 filed June 22, 1984, now abandoned which is a continuation-in-part of application U.S. Ser. No. 519,284 filed Aug. 1, 1983, now abandoned.

The compounds of the instant invention are adenosine analogs having some of the same activities as adenosine, but having a significantly longer duration of action. A distinguishing feature of these compounds from other adenosine analogs previously described, is the discovery that $N^6$-diphenylalkyl adenosines have a favorable ratio of affinities at $A_1$ and $A_2$ receptors and highly desirable central nervous system and cardiovascular activities, such as analgesic, antipsychotic, sedative, antihypertensive, and antianginal.

U.S. Pat. No. 3,590,029 discloses a series of 2-amino-$N^6$-adenosine derivatives which may also include 2-amino-$N^6$-diphenylalkyl adenosines which have circulatory and cardiac activity. German publication No. 2,406,587 discloses and claims $N^6$-diphenylalkyl adenosines as hypolipemic agents.

The present invention relates to a compound of the formula

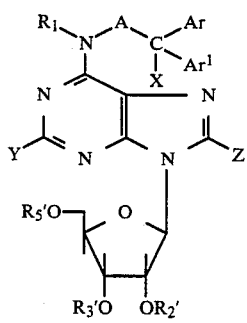

I or a pharmaceutically acceptable addition salt thereof, wherein $R_1$ is hydrogen or lower alkyl; Ar and $Ar^1$ are each independently phenyl, phenyl substituted by halogen, hydroxy, thiol, lower alkoxy, lower thioalkoxy, lower alkanoyloxy, lower alkyl, nitro, amino, lower S(O)n-alkyl, in which n is 0, 1, or 2, sulfonamide or trifluoromethyl, or 2, 3, or 4-pyridyl, 2- or 3-thienyl or -furanyl;

A is straight or branched alkylene of 0 to 8 carbon atoms which may be interrupted by oxygen, sulfur, or NH between carbons 2 and 7 of the alkylene chain; X is hydrogen, hydroxy, lower alkyl, lower carboalkoxy or lower alkanoyloxy; Y is hydrogen, halogen, $NR_2R_3$, $OR_2$, or $SR_2$ in which $R_2$ and $R_3$ are independently hydrogen, lower alkyl or phenyl lower alkyl; Z is hydrogen or halogen; $R_2'$, $R_3'$, and $R_5'$ are each independently hydrogen, alkanoyl having two to twelve carbon atoms in a straight or branched alkyl chain which may be substituted by amino, benzoyl or benzoyl substituted by lower alkyl, lower alkoxy, halogen or trifluoromethyl; additionally, $R_2'$ and $R_3'$ may be linked together to form a five-membered alkylidene ring having a total of up to twenty carbons such as, for example, isopropylidene, and $R_5'$ may be a phosphate, hydrogen or dihydrogen phosphate, or an alkali metal or ammonium or dialkali or diammonium salt thereof, such as, for example, $PO_3Na_2$.

The present invention also relates to a pharmaceutical composition comprising a therapeutically effective amount of a compound of the above formula I with a pharmaceutically acceptable carrier, and to a method of treating mammals by administering to such mammals a dosage form of a compound of the formula I as defined above.

In the compounds of the formula I, the term "lower alkyl" is meant to include a straight or branched alkyl group having from 1 to 6 carbon atoms such as, for example, methyl, ethyl, propyl, isopropyl, butyl, sec-butyl, isobutyl, tert-butyl, amyl, isoamyl, neopentyl, hexyl, and the like.

Halogen includes particularly fluorine, chlorine or bromine.

Lower alkoxy and thioalkoxy are O-alkyl or S-alkyl of from 1 to 6 carbon atoms as defined above for "lower alkyl".

Lower alkanoyloxy is a straight or branched

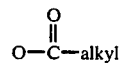

group of from 1 to 6 carbon atoms in the alkyl chain as defined above.

Lower carboalkoxy is a straight or branched

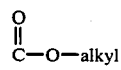

group of from 1 to 6 carbon atoms in the alkyl chain defined above. The compounds of formula I are useful both in the free base form and in the form of acid addition salts. Both forms are within the scope of the invention. In practice, use of the salt form amounts to use of the base form. Appropriate pharmaceutically acceptable salts within the scope of the invention are those derived from mineral acids such as hydrochloric acid and sulfuric acid; and organic acids such as ethanesulfonic acid, benzenesulfonic acid, p-toluenesulfonic acid, and the like, giving the hydrochloride, sulfamate, ethenesulfonate, benzenesulfonate, p-toluenesulfonate, and the like, respectively.

The acid addition salts of said basic compounds are prepared either by dissolving the free base in aqueous or aqueous alcohol solution or other suitable solvents containing the appropriate acid and isolating the salt by evaporating the solution, or by reacting the free base and acid in an organic solvent, in which case the salt separates directly or can be obtained by concentration of the solution.

The compounds of the invention may contain an asymmetric carbon atom at the carbon atom connecting groups A, Ar, $Ar^1$ and X when Ar and $Ar^1$ are different. The invention includes the individual enantiomers, the pure S, the pure R isomer, and mixtures thereof. The individual enantiomers may be prepared or isolated by methods known in the art.

A preferred embodiment of the present invention includes a compound of formula I wherein $R_1$ and X are hydrogen or methyl; $R_2'$ and $R_3'$ are hydrogen, acetyl, benzoyl or when taken together form isopropylidene; $R_5'$ is hydrogen, phosphate, hydrogen phosphate, dihydrogen phosphate, sodium or disodium phosphate; Z is hydrogen or fluorine, and Y, Ar, and $Ar^1$ are as defined above.

Another preferred embodiment of the present invention is a compound of formula I wherein $R_1$, $R_2'$, $R_3'$, $R_5'$, X, and Z are hydrogen, and A, Y, Ar and $Ar^1$ are as defined above.

Another preferred embodiment is a compound of formula I wherein $R_1$, $R_2'$, $R_3'$, $R_5'$, Z, and X are hydrogen; Y is hydrogen, halogen, or $NR_2R_3$ where $R_2$ and $R_3$ are independently hydrogen, lower alkyl or phenyl lower alkyl, and A, Ar and $Ar^1$ are as defined above.

Still another preferred embodiment is a compound of formula I wherein $R_1$, $R_2'$, $R_5'$, Z, and X are hydrogen; Y is hydrogen, chlorine or amino; A is straight or branched alkylene from 1 to 4 carbon atoms, and Ar and $Ar^1$ are as defined above.

A further preferred embodiment is a compound of formula I wherein $R_1$, $R_2'$, $R_3'$, $R_5'$, Z, and X are hydrogen; Y is hydrogen, chlorine or amino; A is methylene and Ar and $Ar^1$ are phenyl.

Particular embodiments include $N^6$-(2,2-diphenylethyl)adenosine; $N^6$-(2,2-diphenylethyl)-2-chloroadenosine, $N^6$-(2,2-diphenylethyl)-2-aminoadenosine, and $N^6$-(2,2-diphenylpropyl)adenosine.

The compounds of formula I may be conveniently synthesized by reacting a 6-halopurine riboside of formula II with the requisite diaryl alkyl amine of formula III in an inert solvent such as alcohol, or an aprotic solvent such as dimethylformamide between about 25° to about 130° C. for from 1–48 hours. It is useful to add a base such as triethylamine, or calcium carbonate to neutralize the hydrogen halide formed as a byproduct of the reaction, but this can also be accomplished by using an extra equivalent of the aryl alkylamine. It is also convenient, although not necessary, to protect the ribofuranose hydroxyl groups as acetate or benzoate esters which can be removed with ammonium hydroxide or sodium methoxide following the synthesis of the $N^6$-substituted adenosine. The reaction is illustrated as follows:

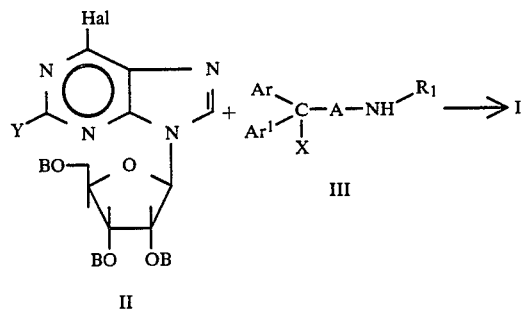

wherein B is H, acetyl or benzoyl; Hal is halogen, preferably chlorine or bromine, and Y, Ar, $Ar^1$, X, A, and $R_1$ are as defined for formula I.

In addition, compounds of formula I wherein Y is other than hydrogen or halogen, may also be prepared from 2,6-dichloropurine riboside triacetate of formula IV in a stepwise manner, by first reacting a compound of the formula IV with the requisite diphenyl alkyl amine of formula IV with the requisite diphenyl alkyl amine of formula III to give a compound of formula V, followed by replacing the chlorine atom at $C_2$ with the group Y using nucleophilic displacement conditions, and removing the acetate protecting groups as illustrated below.

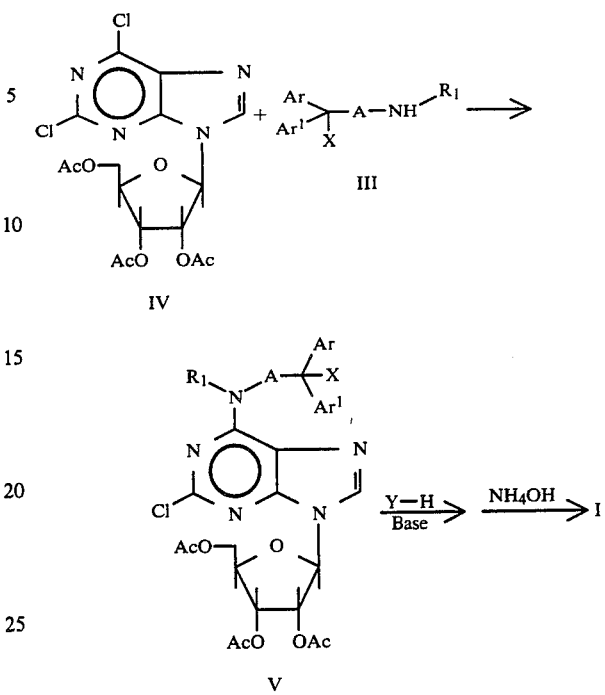

The compounds of formula I have been found to possess differing affinities for adenosine receptors (designated $A_1$ and $A_2$ receptors for convenience). These compounds are active in animal tests which are predictive of neuroleptic activity for the treatment of major psychoses such as schizophrenia. The compounds of the invention also have sedative/hypnotic properties and as such, are useful for the treatment of sleep disorders. These compounds also have analgesic properties and as such, are useful in the treatment of pain.

In addition, the compounds of the present invention are useful as antihypertensive agents for the treatment of high blood pressure. They also increase coronary blood flow and as such are useful in the treatment of angina and myocardial ischemia.

PHARMACOLOGICAL EVALUATION

Adenosine Receptor Binding—$A_1$ Receptor Affinity (RBA1)

Preparation of Membranes

Whole brain minus cerebellum and brainstem from male Long Evans rats (150–200 g) was homogenized in 30 volumes of ice-cold 0.05M Tris-HCl buffer pH 7.7 using a Brinkman Polytron PT-10, (setting number 6 for 20 seconds) and centrifuged for ten minutes at 20,000×g (Sorvall RC-2), 4° C. The supernatant was discarded, and the pellet was resuspended and centrifuged as before. The pellet was resuspended in 20 ml Tris-HCl buffer containing two International Units/ml of adenosine deaminase (Sigma type III from calf intestinal mucosa), incubated at 37° C. for 30 minutes, then subsequently at 0° C. for ten minutes. The homogenate was again centrifuged, and the final pellet was resuspended in ice-cold 0.05M Tris-HCl buffer pH 7.7 to a concentration of 20 mg/ml original wet tissue weight and used immediately.

Assay Conditions

Tissue homogenate (10 mg/ml) was incubated in 0.05M Tris-HCl buffer pH 7.7 containing 1.0 nM [$^3$H]-

N6-cyclohexyladenosine[3H]-CHA) with or without test agents in triplicate for one hour at 25° C. Incubation volume was 2 ml. Unbound [3H]-CHA was separated by rapid filtration under reduced pressure through Whatman glass fiber (GF/B) filters. The filters were rinsed three times with 5 ml of ice cold 0.05M Tris-HCl buffer pH 7.7. The radio-labeled ligand retained on the filter was measured by liquid scintillation spectrophotometry after shaking the filters for one hour or longer on a mechanical shaker in 10 ml of Beckman Ready-Solv HP scintillation cocktail.

Calculations

Nonspecific binding was defined as the binding which occurred in the presence of 1 mM theophylline. The concentration of test agent which inhibited 50% of the specific binding ($IC_{50}$) was determined by nonlinear computer curve fit. The Scatchard plot was calculated by linear regression of the line obtained by plotting the amount of radioligand bound (pmoles/gram of tissue)

$$\text{versus} \left[ \frac{\text{bound radioligand}}{\text{free radioligand}} \right].$$

Since the amount of radioligand bound was a small fraction of the total amount added, free radioligand was defined as the concentration (nM) of radioligand added to the incubation mixture. The Hill coefficient was calculated by linear regression of the line obtained by plotting the log of the bound radioligand vs the log of the $$\left[ \frac{\text{bound radioligand}}{B_{max} - \text{bound radioligand}} \right].$$

The maximal number of binding sites ($B_{max}$) was calculated from the Scatchard plot.

Adenosine Receptor Binding—$A_2$ Receptor Affinity (RBA2)

Tissue Preparation

Brains from 200–500 g mixed sex Sprague-Dawley rats were purchased from Pel-Freez (Rogers, Ark.). Fresh brains from male Long-Evans hooded rats (Blue Spruce farms, Altamont, NY) gave essentially identical results. Brains were thawed and then kept on ice while the striata were dissected out. Striata were disrupted in 10 vol of ice-cold 50 mM Tris.HCl (pH 7.7 at 25° C., pH 8.26 at 5° C.) (Tris) for 30 seconds in a Polytron PT-10 (Brinkmann) at setting 5. The suspension was centrifuged at 50,000 xg for ten minutes, the supernatant discarded, the pellet resuspended in 10 vol ice-cold Tris as above, recentrifuged, resuspended at 1 g/5 ml, and stored in plastic vials at −70° C. (stable for at least six months). When needed, tissue was thawed at room temperature, disrupted in a Polytron, and kept on ice until used.

Incubation Conditions

All incubations were for 60 minutes at 25° C. in 12×75 mm glass tubes containing 1 ml Tris with 5 mg original tissue weight of rat weight of rat striatal membranes, 4 nM [3H]-N-ethyl adenosine-5′-carboxamide ([3H]NECA), 50 nM N6-cyclopentyladenosine (to eliminate $A_1$ receptor binding), 10 mM $MgCl_2$, 0.1 units/ml of adenosine deaminase and 1% dimethylsulfoxide. N6-Cyclopentyladenosine was dissolved at 10 mM in 0.02N HCl and diluted in Tris. Stock solutions and dilutions of N6-cyclopentyladenosine could be stored at −20° C. for several months. Test compounds were dissolved at 10 mM in dimethylsulfoxide on the same day as the experiment, and diluted in dimethylsulfoxide to 100× the final incubation concentration. Control incubations received an equal volume (10 μl) of dimethylsulfoxide; the resulting concentration of dimethylsulfoxide had no effect on binding. [3H]NECA was diluted to 40 nM in Tris. The membrane suspension (5 mg/0.79 ml) contained sufficient $MgCl_2$ and adenosine deaminase to give 10 mM and 0.1 units/ml, respectively, final concentration in the incubation. For test compounds with $IC_{50}$ values less than 1 μM, the order of additions was test compound (10 μl), N6-cyclopentyladenosine (100 μl), [3H]NECA (100 μl), and membranes (0.79 ml). For test compounds with $IC_{50}$ values greater than 1 μM and limited water solubility, the order of additions (same volumes) was test compound, membranes, N6-cyclopentyladenosine, and [3H]NECA. After all additions, the rack of tubes was vortexed, and the tubes were then incubated for 60 min at 25° C. in a shaking water bath. The rack of tubes was vortexed an additional time halfway through the incubation.

Incubations were terminated by filtration through 2.4 cm GF/B filters under reduced pressure. Each tube was filtered as follows: the contents of the tube were poured onto the filter, 4 ml of ice-cold Tris were added to the tube and the contents poured onto the filter, and the filter was washed twice with 4 ml of ice-cold Tris. The filtration was complete in about twelve seconds. Filters were put in scintillation vials, 8 ml of Formula 947 scintillation fluid added, and the vials left overnight, shaken, and counted in a liquid scintillation counter at 40% efficiency.

Data Analysis

Nonspecific binding was defined as binding in the presence of 100 μM N6-cyclopentyladenosine, and specific binding was was defined as total binding minus nonspecific binding. The $IC_{50}$ was calculated by weighted nonlinear least squares curve-fitting to the mass-action equation.

$$Y = T - S \cdot \frac{D}{D + K}$$

where
Y is cpm bound
T is cpm total binding without drug
S is cpm specific binding without drug
D is the concentration of drug
and
K is the $IC_{50}$ of the drug Weighting factors were calculated under the assumption that the standard deviation was proportional to the predicted value of Y. Nonspecific binding was treated as a very large (infinite) concentration of drug in the computer analysis.

The $IC_{50}$ values (nM) for adenosine $A_1$ and $AC_2$ receptor affinity are reported in the table.

ANTIPSYCHOTIC EVALUATION

The compounds of the invention are new chemical substances which are useful as pharmaceutical agents for the treatment of psychoses. The antipsychotic activity of representative compounds of the invention was established by the Mouse Activity and Screen Test Procedure (MAST) described below.

Animals

Nine unfasted Swiss-Webster male mice weighing 20-30 g are equally divided into three groups for each drug dose to be tested. That is, data for each dose level was generated by three separate groups of three mice each.

Drugs

A minimum of three dose levels (10, 30, and 100 mg/kg) are tested for each drug. Treatments are administered intraperitoneally one hour prior to testing. All dosages are calculated as parent compound and given in volumes of 10 ml/kg. Compounds are dissolved or suspended in 0.2% Methocel. Control animals are injected with Methocel.

Testing:

A two part testing procedure is started one hour postinjection. First, the screen test (ST) is performed (see *Pharmac. Biochem. Behav.* 6, 351-353, 1977). Briefly this test consists of placing mice on individual wire screens which are then rotated 180 degrees at the start of a 60 second observation period. The number of mice falling off the inverted screen is recorded.

Immediately following the screen test, the final phase of testing is initiated by placing each group of three mice in one actophotometer (*Life Sciences*, 22, 1067-1076, 1978). The actophotometer consists of a cylindrical chamber whose center is occupied by another cylinder which contains the illumination for six photocells located on the perimeter of the chamber. Six light-beam interruptions equal one count. Locomotor activity is recorded by computer at ten minute intervals for 60 minutes.

Data:

The data obtained from the screen test are expressed as percent of mice falling off the screen. Data derived from locomotor activity of drug treated mice are compared to the activity of vehicle treated animals and are expressed as percent inhibition of spontaneous locomotion. All percentages reported for inhibition of locomotion (LI) are based upon data accumulated for one hour. Both phases of testing are graded: A=60-100%; C=31-59%; and N=0-30%. An overall dose rating is obtained by the following criteria:

| Inhibition of Locomotion Rating | with | Screen Test Failure Rating | Dose = Rating |
| --- | --- | --- | --- |
| A | — | N or C | = A |
| A | — | A | = C |
| C | — | N or C | = C |
| | | All other combinations | = N |

LAD refers to the lowest dose at which an A rating is achieved. Compounds which exhibit an overall dose rating of A at a dose of 100 milligrams/kilogram or less are considered active. Utilizing this procedure, an overall dose rating of A was obtained for the noted compound at the indicated dose. The compounds are identified in the Examples.

| Example | Dose (mg/kg) | Inhibition of mouse locomotor activity | Inhibition of screen test failure |
| --- | --- | --- | --- |
| 1 | 10 | 92% | 11% |
| | 30 | 93% | 22% |
| | 100 | 94% | 44% |
| 2 | 10 | −9% | 0% |
| | 30 | 13% | 0% |
| | 100 | 60% | 0% |

-continued

| Example | Dose (mg/kg) | Inhibition of mouse locomotor activity | Inhibition of screen test failure |
| --- | --- | --- | --- |
| 3 | 10 | 56% | 0% |
| | 30 | 85% | 11% |
| | 100 | 92% | 44% |
| 4 | 10 | 64% | 0% |
| | 30 | 87% | 11% |
| | 100 | 95% | 22% |

Representative compounds of the invention (identified in the Examples) were also tested for antipsychotic activity according to the following protocol (SIDR). The noted compound has the indicated $ED_{50}$ values (mg/kg) and is considered active as an antipsychotic agent in the test procedure.

Procedure

Mature male Long-Evans rats or squirrel-monkeys are conditioned to push a lever in order to avoid a painful electric footshock. If the animal fails to push the lever, he receives a shock every ten seconds until the lever is pushed. Shocks can be terminated by pushing the lever. Thereafter, as long as the lever is pushed at least once every 20 seconds, there will be no shock.

Each animal acts as its own control; one weekly session is used to establish baseline behavior and another session later in the week is used as a drug session. Once patterns of avoidance are established, the effects of standard and unknown compounds are studied.

RESPONSE EVALUATION

All events are electronically programmed and the response to these events counted or used as feed-back to the program.

ANTIHYPERTENSIVE EVALUATION (AHP3)

The usefulness of the compounds of the present invention as antihypertensive agents is demonstrated by their effectiveness in standard pharmacological test procedures, for example, in causing a significant decrease in mean arterial blood pressure in the conscious rat. This test procedure is described in the following paragraphs.

A Method for the Direct Monitoring of Aortic Blood Pressure and Heart Rate from Conscious Rats The continuous monitoring of pulsatile blood pressure (BP) from unrestrained conscious rats surgically equipped witth polyethylene cannulas was accomplished by means of a computer assisted data capture scheme (CADCS). The basic elements of the methodology are the cannulation procedure and the CADCS.

Method

Cannulation Procedure:

Rats were anesthetized with Telazol (1:1 tiletamine HCl and zolazepam HCl); 20-40 mg/kg IM and the descending aorta exposed via a midline incision. Cannulas fabricated from polyethylene tubing were inserted into the aorta via an undersized puncture hole below the renal arteries. The puncture hole was made by a 23 G disposable needle with a section of the aorta clamped off above and below the puncture site. The cannulas, consisting of a PE100 (0.86 mm ID) body and a PE50 (0.58 mm ID) tip, were attached to a trocar, inserted through the psoas muscle, and passed subcutaneously along the midline of the back and externalized between the ears. The cannulas were anchored to the psoas muscle and between the scaulae (3-0 green braided suture). The midline incision was closed in two steps (muscle first, skin second) using continuous over-and over sutures (4-0 chronic). Each rat was then given penicillin 30,000 units subcutaneously (Penicillin G Procaine Sterile Suspension).

The rats were fitted with a harness-spring-swivel assembly designed to protect the cannula and to provide the rat relative freedom of movement. The harnesses were fabricated from nylon hook and loop tape cemented to a metal plate to which spring wires (18-8 stainless steel), were attached to brass swivels. Each polyethylene cannula was channeled through a spring and connected through a swivel to a pressure transducer (Model P23Gb; Statham Instruments; Hato Rey, Puerto Rico) and an infusion pump (Sage model 234-7; Orion Research, Cambridge, MA) by means of PE100 tubing. While on test, each rat received a continuous slow infusion of heparinized saline solution (approximately 400 l or 40 units of heparin per 24 hour period) to prevent clot formation. Additional "flushes" of the cannula with heparinized saline were carried out when the aortic pulse pressure (systolic minus diastolic) was less than 25 mm Hg.

CADCS:

The pulsatile blood pressure and heart rate of each of 32 rats was monitored every minute by means of two in-laboratory microcomputers communicating directly with a data concentrator computer. The data were first stored on the data concentrator disk and then transferred to a magnetic tape for analysis and report generation by the main research computer. The overall scheme involved modulating the primary signal from the pressure transducer, generating the primary data set of the one-minute values for systolic, diastolic, and mean blood pressures and heart rate by the in-lab microcomputer and the storage, analysis, and report generation by the main reserach computer.

The transducers were connected to analog signal conditioning modules. The modules provided a regulated excitation voltage for the transducers, amplification as required to interface the microprocessors and an active low pass filter to compensate for the pressure wave form distortion produced by the flexible, fluid filled, narrow cannula. The distortion was 22-26 Hz and this provided a reliable estimate of both systolic and diastolic blood pressure.

The microcomputers (one for each of two groups of 16 rats) were connected to the input components through the module interface units, an analog-to-digital converter for the pressure wave form signal and the digital inputs for the dose and event marker switches. The microcomputer controlled the sequential acquisition of data from the modular interface units through an internal synchronous time-of-day clock/time base generator. Utilizing the time base generator as a reference, the blood pressure values and the marker switch status for each of the 32 stations were sampled every ten msec. The microcomputer processed each blood pressure sample as it was received to produce "running average" values for heart rate, and mean, systolic and diastolic blood pressures.

When tested by the above procedure, compounds of Examples 1 and 3 produced the following changes in MAP and heart rate.

|  | mg/kg | Mμ.c. ↓ | HR ↑ |
|---|---|---|---|
| Example 1 | 1 | 16% | <20% |
|  | 3 | 20% | <20% |
|  | 10 | 20% | <20% |
|  | 30 | 35% | <20% |
| Example 3 | 10 | 15% | <20% |

LAD refers to the lowest dose tested at which a >10% reduction in blood pressure for four consecutive hours is achieved.

CORONARY BLOOD FLOW (PCS2A)

Method

Male rats (400-600 gms) are pretreated with Na heparin 2000 units and anesthetized with Na pentobarbital (50 mg/kg) administered intraperitoneally. Once anesthetized, the rat heart is rapidly excised, the ascending aorta fitted to the aortic perfusion cannula, and secured with a ligature. The coronary arteries are perfused initially at a rate of about 15 ml/min for two to three minutes, afterwhich they are perfused at constant pressure of 70 mm Hg and temperature of 37° C. The electrocardiogram (ECG) is recorded using two platinum electrodes positioned at the base and apex of the left ventricle. A second heart is excised, cannulated, and perfused by the same method outlined above. Both hearts are tested in parallel. The standard physiological salt solution (PSS) is a modified Krebs-Hanseleit bicarbonate buffer of the following composition in mM concentration: NaCl, 127; NaHCO$_3$, 25; dextrose, 5.5; Na Pyruvate, 2.0; KCl, 4.7; MgSO$_4$, 1.1; KH 2PO$_4$, 1.2; CaCl$_2$.2H$_2$O, 2.5; CaNa$_2$ EDTA, 0.05.

A 30-minute stabilization period is observed before starting the test protocol.

Microprocessor Controlled Coronary Perfusion and Drug Delivery System

The microprocessor control system is a servo mechanism which permits coronary perfusion pressure (CPP) and drug concentration to be maintained constant independent of changes in coronary flow. The level at which CPP and drug concentration are maintained can be changed by commands communicated through the microprocessor keyboard. Dose-response curves are carried out by perfusing concentrated drug solution (DC) at rates proportional to total coronary flow (CF$_T$). Drug concentrations are increased by proportionate increases in the rate of DC infusion over CF$_T$ via the microprocessor keyboard. The proportional flow rates for DC:CF$_T$ is about 0.0002:1 at the low end and 0.02:1 at the high end of the dose-response curve. Dose-response curves encompassing at least two log doses are carried out by preparing two DCs with a concentration difference of 1:100. Following the first dose range of two log doses, the DC are switched, proportional pumping rate adjusted, and the dose-response curve continued for another two log doses. The standard dose-response curve is carried out in one-half log dose increments starting at a subthreshold dose and ending at a dose which produces near maximal response in activity. Standard reference compounds are tested over the range of $10^{-9}$ to $10^{-6}$M.

Measurements

Measurements are for heart rate (HR) and coronary flow (CF). Units are: HR, beats/minute (bpm) and CF, milliliters/minute (ml/min). HR is calculated from the ECG strip chart recording and CF is calculated by recording analog outputs from pumps 1 and 2. Outputs from pump #1=$CF_T$ and the output from pump #2=CF for heart B ($CF_B$). CF for heart A ($CF_A$) is calculated ($CF_T - CF_B = CF_A$).

Using the above technique, the effects of the compound of Examples 1 and 2 are as follows:

ing by 50% relative to vehicle controls. $ED_{50}$ values are calculated by nonlinear regression analysis.

The biological data are summarized in the Table. Accordingly, the present invention also includes a pharmaceutical composition for treating psychoses, sleep disorders, pain, hypertension or angina comprising a corresponding antipsychotic, sedative, analgesic, antihypertensive or antianginal effective amount of a compound of the formula I as defined above together with a pharmaceutically acceptable carrier.

TABLE

Biological Test Results

| Example | RBA1 $IC_{50}$ [nM] | RBA2 $IC_{50}$ [nM] | MAST LI LAD (mg/kg) | MAST ST LAD (mg/kg) | SIDR $ED_{50}$ (mg/kg) | AHP3 BP LAD (mg/kg) | PCS2A HR $EC_{50}$ [μM] | PCS2A CF $EC_{50}$ [μM] | AW $ED_{50}$ (mg/kg) |
|---|---|---|---|---|---|---|---|---|---|
| 1 | 11 | 44 | 3 | >100 | 2.5 | 1 | 2 | 1 | 6.9 |
| 2 | 139 | 390 | 100 | >100 |  | >30 | 6 | 3 |  |
| 3 | 67 | 139 | 10 | >100 | 9.6 | 10 | >30 | 30 |  |
| 4 | 89 | 275 | 10 | >100 | 3.8 | 30 | >0.1 | 1 |  |
| 5 | 846 | 5650 | 100 | >100 | >50 | >10 | >3 | >3 |  |
| 6 | 518 | 9520 | 100 | >100 |  | >30 | >1 | 0.014 |  |
| 7 | 147 | 3290 | 100 | >100 |  | >10 | 3 | >3 |  |
| 8 | 66 | 41 | 10 | >100 | 5.6 | 10 | 3 | <0.1 | 10.58 |
| 9 | 13 | 17 | ≦10 | 100 |  |  |  |  |  |
| 10 | 14 | 71 | 3 | >100 | 8.6 | 10 | 1.4 | 0.01 |  |
| 11 | 69 | 210 | 30 | >100 |  | 10 | >3 | 0.05 |  |
| 12 | 94 | 303 | 30 | >100 |  | 10 | >10 | >10 |  |
| 13 | 16 | 94 | 3 | >100 |  | 10 |  |  |  |
| 14 |  |  | 1 | >100 |  |  |  |  |  |
| 15 | 27 | 90 | 10 | >100 | 12.7 | 10 | >3 | 0.03 |  |
| 16 | 223 | 319 | 100 | >100 |  | >10 |  |  |  |

Example (PD Number)

| | RBA1 $IC_{50}$ [nM] | RBA2 $IC_{50}$ [nM] | MAST LI LAD (mg/kg) | MAST ST LAD (mg/kg) | SIDR $ED_{50}$ (mg/kg) | AHP3 BP LAD (mg/kg) | PCS2A HR $EC_{50}$ [μM] | PCS2A CF $EC_{50}$ [μM] | AW $ED_{50}$ (mg/kg) |
|---|---|---|---|---|---|---|---|---|---|
| 17 | 512 | 713 | 100 | >100 |  |  | >3 | >3 |  |
| 18 | 1925 | 2120 | >30 | >30 |  | >10 |  |  |  |
| 19 | 21 | 56 | 10 | 30 |  | 10 | >3 | 0.03 |  |
| 20 | 229 | 559 | 100 | >100 |  | >10 | >3 | 0.3 |  |
| 21 | 285 | 470 | 30 | >100 |  | >10 | >10 | >10 |  |
| 22 | 12 | 94 | 1 | 100 |  | 10 | 0.5 | >1 |  |
| 23 | 69 | 293 | 3 | >100 |  | >10 | ~1 | >3 |  |
| 24 | 79 | 4600 | 30 | >30 |  |  | 3 | >3 |  |
| 25 | 53 | 166 | 3 | >100 | 11.3 | 10 | 2.2 | 1 |  |
| 26 | 1230 | 3840 | 10 | >100 |  | 10 |  |  |  |
| 27 | 30900 | 6820 | 30 | >100 |  |  |  |  |  |
| 28 |  | ~20 | ≦3 | >30 |  |  |  |  |  |
| 29 | 242 | 919 | 30 | >100 |  | 10 |  |  |  |

| Dose (Molar) | Example 1 CF | Example 1 HR | Example 2 CF | Example 2 HR |
|---|---|---|---|---|
| 1 × 10⁻⁹ | 7% | 1% |  |  |
| 3 × 10⁻⁹ | 15% | 3% |  |  |
| 1 × 10⁻⁸ | 32% | −1% | 26% | −2% |
| 1 × 10⁻⁷ | 43% | −13% | 42% | −5% |
| 1 × 10⁻⁶ | 50% | −47% | 47% | −19% |
| 3 × 10⁻⁶ |  |  | 48% | −34% |

ANALGESIC EVALUATION

The antiwrithing (AW) test provides preliminary assessment of compounds with potential analgesic activity. The test is performed in male Swiss-Webster mice. Compounds are administered subcutaneously in aqueous 0.2% methylcellulose or other appropriate vehicles in volumes of 10 ml/kg. Dosages represent active moiety.

Acetic acid (0.6%, 10 ml/kg) is injected intraperitoneally 20 minutes after administration of the adenosine agonist. Writhing movements are counted for five minutes starting seven minutes after the acetic acid injection. Writhing is defined as abdominal constriction and stretching of the body and hind legs with concave arching of the back. Data are expressed as $ED_{50}$ values, where the $ED_{50}$ is the dose necessary to suppress writh- The present invention further includes a method for treating psychoses, sleep disorders, pain, hypertension, or angina in mammals suffering therefrom comprising administering to such mammals either orally or parenterally a corresponding pharmaceutical composition containing a compound of the formula I as defined above in appropriate unit dosage form.

For preparing pharmaceutical compositions from the compounds described by this invention, inert, pharmaceutically acceptable carriers can be either solid or liquid. Solid form preparations include powders, tablets, dispersible granules, capsules, cachets, and suppositories. A solid carrier can be one or more substances which may also act as diluents, flavoring agents, solubilizers, lubricants, suspending agents, binders or tablet disintegrating agents; it can also be encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 or 10 to about 70 percent of the active ingredient. Suitable solid carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby to solidify.

Liquid form preparations include solutions, suspensions, and emulsions. As an example may be mentioned water or water propylene glycol solutions for parenteral injection. Liquid preparations can also be formulated in solution in aqueous polyethylene glycol solution. Aqueous solutions suitable for oral use can be prepared by dissolving the active component in water and adding suitable colorants, flavors, stabilizing and thickening agents as desired. Aqueous suspensions suitable for oral use can be made by dispersing the finely divided active component in water with viscous material, i.e., natural or synthetic gums, resins, methylcellulose, sodium carboxymethylcellulose, and other well-known suspending agents.

Also included are solid form preparations which are intended to be converted, shortly before use, to liquid form preparations for either oral or parenteral administration. Such liquid forms include solutions, suspensions, and emulsions. These particular solid form preparations are most conveniently provided in unit dose form and as such are used to provide a single liquid dosage unit. Alternately, sufficient solid may be provided so that after conversion to liquid form, multiple individual liquid doses may be obtained by measuring predetermined volumes of the liquid form preparation as with a syringe, teaspoon, or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solubilizing agents, and the like. The liquid utilized for preparing the liquid form preparation may be water, isotonic water, ethanol, glycerine, propylene glycol, and the like as well as mixtures thereof. Naturally, the liquid utilized will be chosen with regard to the route of administration, for example, liquid preparations containing large amounts of ethanol are not suitable for parenteral use.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampoules. The unit dosage form can also be a capsule, cachet, or tablet itself or it can be the appropriate number of any of these in packaged form.

The quantity of active compound in a unit dose of preparation may be varied or adjusted from 1 mg to 500 mg preferably to 5 to 100 mg according to the particular application and the potency of the active ingredient. The compositions can, if desired, also contain other compatible therapeutic agents.

In therapeutic use as described above, the mammalian dosage range for a 70 kg subject is from 0.1 to 150 mg/kg of body weight per day or preferably 1 to 50 mg/kg of body weight per day. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter the dosage is increased by small increments until the optimum effect under the circumstances is reached. For convenience, the total daily dosage may be divided and administered in portions during the day if desired.

The following Examples further illustrate the invention.

EXAMPLE 1

$N^6$-(2,2-Diphenylethyl)adenosine

A solution of 6-chloro-9-$\beta$-D-ribofuranosylpurine (11.47 g, 0.04 mol) and 2,2-diphenylethylamine (19.73 g, 0.10 mol, 250 mol%) in absolute ethanol (300 ml) is heated at reflux under nitrogen with magnetic stirring for three days, during which time the starting material is consumed according to TLC analysis (5/1 CHCl$_3$/MeOH). The cooled reaction mixture is evaporated in vacuo to a gummy foam which is dissolved in ethyl acetate. Two crops of crystals are obtained and discarded. The filtrate is diluted with hexane, the resulting oil is separated, and the remainder is evaporated in vacuo to a white foam. Neither the oil nor the foam crystallizes well from ethyl acetate/hexane, ethyl acetate alone, or ethanol/water, but crystallization of the combined oil and foam twice from methanol affords $N^6$-(2,2-diphenylethyl)adenosine as a white solid, mp 106.6°–115° C. (after recrystallization from methanol).

Anal. Calcd. for $C_{24}H_{25}N_5O_4$0.3H$_2$O; C, 63.64, H, 5.71, N, 15.47, Cl, 0.00, H$_2$O, 1.19. Found: C, 63.97; H, 5.48, N, 15.48, halogen (total), 0.00, H$_2$O (Karl Fisher) 1.44.

EXAMPLE 2

$N^6$-(3,3-Diphenylpropyl)adenosine

A solution of 6-chloro-9-$\beta$-D-ribofuranosylpurine (2.87 g, 0.010 mol) and 3,3-diphenylpropylamine (5.28 g, 0.025 mol, 250 mol%) in absolute ethanol (75 ml) is heated at reflux for six days, during which time the starting material is mostly consumed according to TLC analysis (5/1 CHCl$_3$/MeOH). The solution is cooled to 5° C. and the resulting first and second crops of white crystals are combined to give $N^6$-(3,3-diphenylpropyl)adenosine, mp 103°–118° C. (from absolute ethanol).

EXAMPLE 3

$N^6$-(2,2-Diphenylethyl)-2-chloroadenosine

A mixture of 2.75 g of triacetyl-2,6-dichloro-9-($\beta$-D-ribofuranosyl)purine (M. J. Robins and B. Uznanski Can. J. Chem., 59, 2601 (1981), J. F. Gerster and R. K. Robins, J. Org. Chem., 31, 3528 (1966)), 1.34 g of 2,2- diphenylethylamine and 0.748 g of triethylamine is stirred at room temperature, under a nitrogen atmosphere for four hours in 50 ml of 1,2-dimethoxyethane (distilled over NaH). The precipitate of $Et_3N^+HCl$ is filtered and the solvent is evaporated from the filtrate to dryness. The residue is dissolved in 50 ml of methanol saturated with ammonia and stirred at room temperature for three hours. The mixture is evaporated to dryness and the residue is purified by medium pressure liquid chromatography on silica gel using 5% methanol in chloroform as the eluent. Evaporation of the solvent from the pure fractions affords a solid material which is crystallized from a mixture of chloroform-2-propanol (10:1) and hexane yielding $N^6$-(2,2-diphenylethyl)-2-chloroadenosine, mp 120°–123° C.

Anal. Calcd. for: $C_{24}H_{24}N_5O_4Cl$: C, 59.81; H, 5.01; N, 14.53; Cl, 7.35. Found: C, 59.52; H, 5.20; N, 14.27, Cl, 7.05.

EXAMPLE 4

$N^6$-(2,2-Diphenylethyl)-2-aminoadenosine

A mixture of 1.25 g of 6-chloro-2-amino-9-($\beta$-D-ribofuranosyl)purine, 0.899 g of 2,2-diphenylethylamine and 0.503 g of triethylamine is heated under reflux in 30 ml of absolute ethanol under a nitrogen atmosphere for 18 hours. The solvent is evaporated to dryness and residue is treated with 50 ml of cold water. The insoluble organic material is filtered, dried, and purified by medium pressure liquid chromatography on silica gel. The product is eluted with 10% methanol-chloroform. Evaporation of the solvent from the pure fractions affords a colorless solid material. Crystallization from a mixture of $CHCl_3$-2-propanol (10:1) and hexane affords $N^6$-(2,2-diphenylethyl)-2-aminoadenosine, mp 134°–137° C.

Anal. Calcd. for $C_{24}H_{26}N_6O_4$: C, 62.32; H, 5.66; N, 18.17. Found: C, 62.18; H, 5.53; N, 17.88.

EXAMPLE 5

$N^6$-Diphenylmethyladenosine

The title compound is prepared essentially as described in Example 1, substituted diphenylmethylamine for 2,2-diphenylethylamine, and substituting isopropyl alcohol for ethanol; mp 89°–96° C.

Anal. Calcd. for $C_{23}H_{23}N_5O_4$: C, 63.73; H, 5.35; N, 16.16. Found: C, 64.97; H, 5.49; N, 14.94.

EXAMPLE 6

$N^6$-(4,4-Diphenylbutyl)adenosine

The title compound is prepared essentially as described in Example 1, substituting 4,4-diphenylbutylamine hydrobromide for 2,2-diphenylethylamine; mp 102°–108° C.

Anal. Calcd. for $C_{26}H_{29}N_5O_4.0.6H_2O.0.3C_2H_6O$ (ethanol): C, 63.88; H, 6.45; N, 14.00. Found: C, 63.92; H, 6.44; N, 13.99.

EXAMPLE 7

$N^6$-(5,5-Diphenylpentyl)adenosine

The title compound is prepared essentially according to Example 1, substituting 5,5-diphenylpentylamine hydrogen sulfate for 2,2-diphenylethylamine, and using triethylamine as base; mp 78°–82° C.

Anal. Calcd. for $C_{27}H_{31}N_5O_4.H_2O$: C, 63.43; H, 6.53; N, 13.70. Found: C, 63.43; H, 6.59; N, 13.75.

EXAMPLE 8

$N^6$-(2,2-Diphenylpropyl)adenosine

A mixture of 6-chloro-9-$\beta$-D-ribofuranosylpurine (2.32 g, 8.09 mmol), 2,2-diphenylpropylamine hydrochloride (2.01 g, 100 mol%) and triethylamine (2.3 mL, 204 mol%) in N,N-dimethylformamide (30 mL) is stirred under nitrogen at room temperature for 19 days, filtered, the solid is washed with ether, and the filtrate is evaporated to an oil. The oil is purified by column chromatography over silica gel, eluting with 5/1 chloroform/methanol, and the appropriate fractions are evaporated to afford $N^6$-(2,2-diphenylpropyl)adenosine as a foam which retains one-half mole of N,N-dimethylformamide.

Anal. Calcd. for $C_{25}H_{27}N_5O_4.0.5C_3H_7NO$: C, 63.90; H, 6.18; N, 15.47. Found: C, 63.90; H, 6.07; N, 15.45.

EXAMPLE 9

$N^6$-(2-(3-Methylphenyl)-2-phenylethyl)adenosine

The title compound is prepared essentially as described in Example 1, substituting 2-(3-methylphenyl)-2-phenylethylamine for 2,2-diphenylethylamine, mp 92°–105° C.

Anal. Calcd. for $C_{25}H_{27}N_5O_4$: C, 65.06; H, 5.90; N, 15.17. Found: C, 65.49; H, 5.94; N, 14.38.

EXAMPLE 10

$N^6$-(2-(4-Fluorophenyl)-2-phenylethyl)adenosine

The title compound is prepared as a tan foam essentially according to the method described in Example 8, substituting 2-(4-fluorophenyl)-2-phenylethylamine for 2,2-diphenyl propylamine hydrochloride.

Anal. Calcd. for $C_{24}H_{24}N_5O_4F.0.2H_2O$: C, 61.45; H, 5.25; N, 14.93. Found: C, 61.43; H, 5.41; N, 14.98.

EXAMPLE 11

$N^6$-(2-(4-Fluorophenyl)-2-phenylethyl)-2-chloroadenosine

The title compound is prepared essentially as described in Example 3, substituting 2-(4-fluorophenyl)-2-phenylethylamine for 2,2-diphenylethylamine; mp 120°–123° C.

Anal. Calcd. for $C_{24}H_{23}N_5O_4ClF$: C, 57.66; H, 4.63; N, 14.00; Cl, 7.09; F, 3.80. Found: C, 57.63; H, 4.92; N, 13.76; Cl, 6.95; F, 3.99.

EXAMPLE 12

$N^6$-(2-(4-Fluorophenyl)-2-phenylethyl)-2-amino adenosine

The title compound is prepared essentially as described in Example 4, substituting 2-(4-fluorophenyl)-2-phenylethylamine for 2,2-diphenylethylamine; mp 127°–130° C.

Anal. Calcd. for $C_{24}H_{25}N_6O_4F.0.65H_2O$: C, 58.56; H, 5.38; N, 17.07; F, 3.86. Found: C, 58.95; H, 5.73; N, 16.62; F, 3.95.

EXAMPLE 13

$N^6$-(2,2-Di-(4-fluorophenyl)ethyl)adenosine

The title compound is prepared essentially as described in Example 1, substituting 2,2-di-(4-fluorophenyl)ethylamine for 2,2-diphenylethylamine, and using triethylamine as base; mp 75°–80° C.

EXAMPLE 14

N$^6$-(2-(3-Chlorophenyl)-2-phenylethyl)adenosine

The title compound is prepared essentially according to Example 1, substituting 2-(3-chlorophenyl)-2-phenylethylamine hydrochloride for 2,2-diphenylethylamine, and using triethylamine as base; mp 107°–110° C.

EXAMPLE 15

N$^6$-(2-(4-Chlorophenyl)-2-phenylethyl)adenosine

The title compound is prepared essentially as described in Example 1, substituting 2-(4-chlorophenyl)-2-phenylethylamine hydrochloride for 2,2-diphenylethylamine, and using triethylamine as base; mp 89°–95° C.

EXAMPLE 16

N$^6$-(2-(4-Chlorophenyl)-2-phenylethyl-2-aminoadenosine

The title compound is prepared essentially as described in Example 4, substituting 2-(4-chlorophenyl)-2-phenylethylamine hydrochloride for 2,2-diphenylethylamine; mp 134°–137° C.

Anal. Calcd. for $C_{24}H_{25}N_6O_4Cl.0.6H_2O$: C, 56.77; H, 5.20; N, 16.55. Found: C, 56.42; H, 4.99; N, 16.30.

EXAMPLE 17

N$^6$-(2,2-Di(4-chlorophenyl)ethyl)adenosine

The title compound is prepared essentially as described in Example 1, substituting 2,2-di(4-chlorophenyl)ethylamine for 2,2-diphenylethylamine, and using triethylamine as base; mp 95°–120° C.

EXAMPLE 18

N$^6$-(2,2-Di-(4-chlorophenyl)ethyl-2-aminoadenosine

The title compound is prepared essentially as described in Example 4, substituting 2,2-di-(4-chlorophenyl)ethylamine for 2,2-diphenylethylamine; mp 128°–130° C.

Anal. Calcd. for $C_{24}H_{24}N_6O_4Cl_2$: C, 54.24; H, 4.55; N, 15.81; Cl, 13.34. Found: C, 54.21; H, 4.70; N, 15.55; Cl, 13.10.

EXAMPLE 19

N$^6$-(2-(4-Methoxyphenyl)-2-phenylethyl)adenosine

The title compound is prepared essentially as described in Example 1, substituting 2-(4-methoxyphenyl)-2-phenylethylamine hydrochloride for 2,2-diphenylethylamine, and using triethylamine as base; mp 87°–92° C.

EXAMPLE 20

N$^6$-(2,2-Di-(4-nitrophenyl)ethyladenosine

The title compound is prepared essentially as described in Example 1, substituting 2,2-di-(4-nitrophenyl)ethylamine hydrochloride for 2,2-diphenylethylamine, and using triethylamine as base; mp 121°–124° C.

Anal. Calcd. for $C_{24}H_{23}N_7O_8$: C, 52.62; H, 4.40; N, 17.94. Found: C, 52.74; H, 4.42; N, 17.94.

EXAMPLE 21

N$^6$-(2,2-Diphenylpropyl)-2-aminoadenosine

The title compound is prepared essentially as described in Example 4, substituting 2,2-diphenylpropylamine for 2,2-diphenylethylamine; mp 129°–132° C.

EXAMPLE 22

N$^6$-(2,2-Diphenyl-2-hydroxyethyl)adenosine

The title compound is prepared as a pale yellow foam which retains 0.3 mol dimethylformamide essentially according to the method described in Example 8, substituting 1,1-diphenyl-2-hydroxyethylamine hydrochloride for 2,2-diphenylpropylamine hydrochloride.

Anal. Calcd. for $C_{24}H_{24}N_5O_5.0.3C_3H_7NO$: C, 61.60; H, 5.64; N, 15.30. Found: C, 61.30; H, 5.63; N, 15.09.

EXAMPLE 23

N$^6$-(2,2-Diphenyl-2-hydroxyethyl)-2-aminoadenosine

The title compound is prepared essentially as described in Example 4, substituting 2,2-diphenyl-2-hydroxyethylamine for 2,2-diphenylethylamine; mp 138°–140° C.

EXAMPLE 24

N$^6$-(2-Carbomethoxy-2,2-diphenylethyl)adenosine

The title compound is prepared as a yellow oil essentially according to the method described in Example 8, substituting 2-carbomethoxy-2,2-diphenylethylamine hydrochloride for 2,2-diphenylpropylamine hydrochloride.

EXAMPLE 25

2',3',5'-Tri-O-acetyl-N$^6$-(2,2-diphenylethyl)adenosine

N$^6$-(2,2-Diphenylethyl)adenosine (4.6 g, 0.01 mole) and acetic anhydride (2.9 mL, 306 mol%) are mixed in pyridine at room temperature under nitrogen for 20 hours, and the reaction is evaporated in vacuo. The residue is dissolved in chloroform, washed twice with aqueous ice-cold 5% sodium carbonate, and the organic layer is dried (MgSO$_4$) and evaporated in vacuo. Chromatography over silica gel eluting with 5/1 chloroform/methanol affords the title compound after evaporation in vacuo of appropriate fractions; mp 75°–80° C.

Anal. Calcd. for $C_{30}H_{31}N_5O_7$: C, 62.82; H, 5.45; N, 12.21. Found: C, 62.97; H, 5.57; N, 12.59.

EXAMPLE 26

2',3',5'-Tri-O-benzoyl-N$^6$-(2,2-diphenylethyl)adenosine

The title compound is prepared essentially as described in Example 25, substituting benzoyl chloride for acetic anhydride; mp 60°–75° C.

EXAMPLE 27

2',3',5'-Tri-O-acetyl-N$^6$-(2,2-diphenylethyl)-2-chloroadenosine

A mixture of 2',3',5'-tri-O-acetyl-2,6-dichloro-9-β-D-ribofuranosylpurine (5.25 g, 0.011 mole), 2,2-diphenylethylamine (2.55 g, 0.013 mole) and triethylamine (1.42 g, 0.014 mole) is stirred at room temperature in dry 1,2-dimethoxyethane (100 ml) for four hours. The mixture is filtered and the filtrate is evaporated. The residue is purified by silica gel chromatography eluting with ethyl acetate, and evaporation of the appropriate fractions affords the title compound; mp 68°–71° C.

Anal. Calcd. for $C_{30}H_{30}N_5O_7Cl$: C, 59.26; H, 4.97; N, 11.51; Cl, 5.83. Found: C, 59.23; H, 5.09; N, 11.29; Cl, 5.88.

EXAMPLE 28

$N^6$-(2,2-Diphenylethyl)adenosine-5'-phosphate

A mixture of trimethylphosphate (60 ml) and phosphoryl chloride (1.8 ml) is stirred for several minutes and then cooled to 0° C. To this is added $N^6$-(2,2-diphenylethyl)adenosine (4 g). After six hours at 0° C., the mixture is added to ice water (0.4 L) and stirred for 30 minutes. The precipitate is filtered and the filtrate is adjusted to pH 2 with aqueous 1M sodium hydroxide. The latter is applied to a charcoal-Celite column (30 g each) prepared as an aqueous slurry, and eluted first with water (1 L) and then with 50/2/48 ethanol/ammonia/water (1 L). Further purification over a Biobeads column eluting with 4/1 methanol/water affords the title compound as the sodium, ammonium salt (mp 140°-145° C. decomp). Purification of the initial precipitate over Biobeads as described above affords the title compound as the free acid (mp 157°-160° C.).

Sodium, ammonium salt:
Anal. Calcd. for $C_{24}H_{28}N_6O_7PNa.0.5H_2O$: C, 50.00; H, 5.21; N, 14.58. Found: C, 49.86; H, 5.56; N, 14.33.
Free acid:
Anal. Calcd. for $C_{24}H_{26}N_5O_7P.2H_2O$: C, 51.15; H, 5.33; N, 12.43. Found: C, 51.01; H, 4.85; N, 12.03.

EXAMPLE 29

2',3'-O-Isopropylidene-$N^6$-(2,2-diphenylethyl)adenosine

A mixture of $N^6$-(2,2-Diphenylethyl)adenosine (2.13 g, 0.005 mole), 2,2-dimethoxypropane (8 mL), and bis-(4-nitrophenyl)phosphate (1.9 g, 120 mol%) in acetone (0.2 L) is stirred at room temperature for 16 hours, diluted with aqueous 5% sodium bicarbonate, and the mixture is evaporated in vacuo. The residue is dissolved in water, extracted five times with methylene chloride, and the combined organic layers are dried (MgSO$_4$) and evaporated in vacuo to a foam. A solution of the foam in 1/1 methanol/water is treated batchwise with Bio-Rex AG1X8, and filtration and evaporation of the filtrate affords the title compound; mp 86°-91° C.

Except for those amine sidechains described in further detail below, all can be obtained commercially or are known in the literature.

See: C. Kaiser, et al., *J. Med. Pharm. Chem.* 1962, 5, 1243; K. P. Bogeso, *J. Med. Chem.* 1983, 26, 935; B. Blank, et al., *J. Med. Chem.* 1969, 12, 271; W. A. Zuccarello, et al., *J. Med. Chem.* 1969, 12, 9.

See also: S. Takemura, et al., *Chem. Pharm. Bull.* 1983, 31, 2632.

Additionally, 2-(4-fluorophenyl)-2-phenylethylamine and 2,2-di-(4-fluorophenyl)ethylamine hydrochloride are prepared using the above literature methods.

EXAMPLE A

2-Carbomethoxy-2,2-diphenylethylamine hydrochloride

3-Bromopyruvic acid (170 g) is suspended in cold sulfuric acid (0.85 L) and maintained at 0° C. while benzene (0.255 L) is added over 1.5 hours. The temperature is allowed to warm to 35°-36° C. and then kept at 25° C. for three hours. Pouring over crushed ice (4 L) followed by trituration in cold water and recrystallization from 95% ethanol affords 76 g of 3-bromo-2,2-diphenylpropionic acid (mp 201°-202° C.). This acid (75 g) is suspended in benzene and thionyl chloride (55 ml) is added. After refluxing, the mixture is filtered, and the filtrate affords 40 g of the acid chloride (mp 98°-100° C.). The acid chloride is added portionwise to aqueous ammonium hydroxide with stirring and left overnight, with filtration yielding 3-bromo-2,2-diphenylpropionamide. The amide (10 g) is added portionwise with stirring to a solution of sodium (1.5 g) in absolute ethanol (0.2 L), and the resulting solution is heated for one hour on a steam bath. Dilution with water affords a solid (mp >310° C.), 2,2-diphenyl azetidin-2-one. The azetidinone (2 g) is heated at reflux in methanol saturated with HCl (50 ml) affording the title compound after crystallization from methanol/ether (mp 207°-208° C.).

See also: J. Wegmann and H. Dahn *Helv. Chim. Acta* 1946, 29, 415.

EXAMPLE B 2,2-Diphenyl-2-hydroxyethylamine hydrochloride

Treatment of ethyl glycinate hydrochloride (4.5 g) with phenylmagnesium chloride (from 0.39 mole each of bromobenzene and magnesium), as discussed by A. McKenzie and G. O. Wills *J. Chem. Soc.* 1925, 127, 283 (and references cited therein), affords the title compound (mp 191°-193° C.).

EXAMPLE C 4,4-Diphenylbutylamine

To sodium amide (4.0 moles) in liquid ammonia (3 L) is added diphenylmethane (680 g) with stirring. After 45 minutes, a solution of 3-chloropropionitrile (368.6 g) is added as a solution in ether. Ammonium chloride (300 g) is added followed by evaporation of the ammonia, filtration, and distillation of the filtrate. 4,4-Diphenylbutyronitrile (187 g) distils from 155°-165° at 0.9 mm.

To a suspension of lithium aluminum hydride (23 g) in ether (1 L) is added a solution of 4,4-diphenylbutyronitrile in dioxane (6.25 L), dropwise, at a rate causing gentle reflux. The reaction is maintained at reflux for one hour, and then a solution of potassium carbonate (200 g) in water (300 mL) is added dropwise with stirring. The mixture is filtered with a 1/1 dioxane/ether wash, and evaporation in vacuo of the filtrate followed by distillation affords the title compound (76 g), bp 145°-150° C. at 0.6 mm. The free amine is generally converted to the hydrobromide salt prior to use.

EXAMPLE D 2,2-Di-(4-nitrophenyl)ethylamine hydrochloride

To a solution of 2,2-diphenylethylamine (30 g) and triethylamine (18.21 g) in toluene (300 ml) is added a solution of acetyl chloride (14.13 g) in toluene (60 ml). After 20 minutes the toluene is removed under vacuum, and the residue is purified by silica gel chromatography, eluting with ethyl acetate. Evaporation of the appropriate fractions followed by crystallization from chloroform/methanol/hexane affords the acetamide, mp 75°-80° C. To cold concentrated sulfuric acid (60 ml) is added the acetamide (8 g), and the solution is kept at −5° C. A solution of concentrated nitric acid (8 ml) in cold concentrated sulfuric acid (30 ml) is then added slowly to the amide solution with vigorous stirring and maintaining the temperature at −5° C. After the addition is complete, the solution is stirred for 50 minutes, the reaction is poured into ice water, and the precipitate is filtered and dried, affording N-acetyl-2,2di-(4-nitrophenyl)ethylamine.

Conversion of the nitro amide to the title compound follows the procedure of G. A. Dilbeck, et al., J. Org. Chem. 1978, 43, 4593.

EXAMPLE E 5,5-Diphenylpentylamine hydrogen sulfate

Thionyl chloride (8.9 ml) is added slowly to cyclopropyldiphenylcarbinol (25 g) and the mixture is stirred until gas evolution ceases. Vacuum distillation affords 4-chloro-1,1-diphenylbutene. Conversion of the chloride to the cyanide is accomplished using the method of R. A. Smiley and C. Arnold, J. Org. Chem. 1960, 25, 257. The resulting nitrile (14.72 g) is reduced with Raney-Cobalt (4 g) in tetrahydrofuran (150 ml) and triethylamine (4 ml) at 15°-130° C. and 1450-2100 PSIG. The olefinic moiety is then reduced at room temperature in methanol (150 ml) with concentrated sulfuric acid (3.5 ml) and 20% Pd-C (5 g, added portionwise during the course of the reaction) at room temperature and 50 PSIG hydrogen.

See also: Chem. Abstr. 1971, 75, 88289h.

What is claimed is:

1. A method for treating pain in a mammal suffering therefrom, which comprises administering to such mammal an analgesic effective amount of a compound of the formula

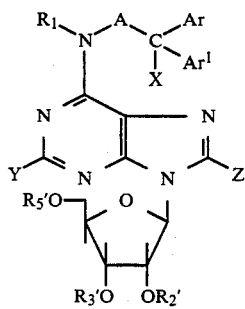

or a pharmaceutically acceptable addition salt thereof, wherein $R_1$ is hydrogen or lower alkyl; Ar and $Ar^1$ are each independently phenyl, phenyl substituted by halogen, hydroxy, thiol, lower alkoxy, lower thioalkoxy, lower alkanoyloxy, lower alkyl, nitro, amino, lower $S(O)_n$-alkyl in which n is zero, one, or two, sulfonamide or trifluoromethyl, or 2-, 3-, or 4-pyridyl, 2- or 3-thienyl or -furanyl; A is straight or branched alkylene of one to eight carbon atoms which may be interrupted by oxygen, sulfur, or NH between two and seven carbons of the alkylene chain; X is hydrogen, hydroxy, lower alkyl, lower carboalkoxy, or lower alkanoyloxy; Y is hydrogen, halogen, $-NR_2R_3$, $-OR_2$ or $-SR_2$ in which $R_2$ and $R_3$ are independently hydrogen, lower alkyl or phenyl lower alkyl; Z is hydrogen or halogen; $R_2'$, $R_3'$, and $R_5'$ are each independently hydrogen, alkanoyl having two to twelve carbon atoms in a straight or branched alkyl chain which may be substituted by amino, benzoyl or benzoyl substituted by lower alkyl, lower alkoxy, halogen, or trifluoromethyl; $R_2'$ and $R_3'$ may be linked together to form a five-membered alkylidene ring having a total of up to twenty carbons, and with the proviso $R_5'$ may also be phosphate, hydrogen phosphate, dihydrogen phosphate, an alkali or dialkali metal phosphate, or ammonium or diammonium phosphate.

2. A method as claimed in claim 1, wherein $R_1$ and X are hydrogen or methyl; $R_2'$ and $R_3'$ are hydrogen, acetyl, benzoyl or when taken together form isopropylidene; $R_5'$ is hydrogen, phosphate, hydrogen phosphate, dihydrogen phsphate, sodium phosphate or disodium phosphate; Z is hydrogen or fluorine.

3. A method as claimed in claim 2, wherein $R_1'$, $R_2'$, $R_3;$, $R_5'$, X, and Z are hydrogen.

4. A method as claimed in claim 3, wherein Y is hydrogen, halogen, or $-NR_2R_3$ where $R_2$ and $R_3$ are independently hydrogen, lower alkyl or phenyl lower alkyl.

5. A method as claimed in claim 3, wherein Y is hydrogen, halogen or $-NR_2R_3$ where $R_2$ and $R_3$ are independently hydrogen, lower alkyl or phenyl lower alkyl.

6. A method as claimed in claim 5, where Y is hydrogen, chlorine or amino and A is straight or branched alkylene from one to four carbon atoms.

7. A method as claimed in claim 6, wherein A is methylene, and Ar and $Ar^1$ are phenyl.

8. A method as claimed in claim 7, and being $N^6$-(2,2-diphenylethyl)adenosine.

9. A method as claimed in claim 7, and being $N^6$-(3,3-diphenylpropyl)adenosine.

10. A method as claimed in claim 7, and being $N^6$-(2,2-diphenylethyl)-2-chloroadenosine.

11. A method as claimed in claim 7, and being $N^6$-(2,2-diphenylethyl)-2-aminoadenosine.

12. A method as claimed in claim 7, and being $N^6$-(2,2-diphenylpropyl)adenosine.

* * * * *

UNITED STATES PATENT AND TRADEMARK OFFICE
CERTIFICATE OF CORRECTION

PATENT NO. : 4,657,897
DATED : April 14, 1987
INVENTOR(S) : James A. Bristol, Walter H. Moos, Bharat Trivedi It is certified that error appears in the above—identified patent and that said Letters Patent is hereby corrected as shown below:

Column 22, line 26: Change "$R_1'$" to --$R_1$--

Column 22, line 27: Change "$R_3;,$" to -- $R_3'$, --

Signed and Sealed this

Eighteenth Day of August, 1987

Attest:

DONALD J. QUIGG

*Attesting Officer*  *Commissioner of Patents and Trademarks*